United States Patent
Jin et al.

(10) Patent No.: US 7,275,932 B2
(45) Date of Patent: Oct. 2, 2007

(54) SELF-CURING SYSTEM FOR ENDODONTIC SEALANT APPLICATIONS

(75) Inventors: Shuhua Jin, Wallingford, CT (US); Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 313 days.

(21) Appl. No.: 10/252,073

(22) Filed: Sep. 20, 2002

(65) Prior Publication Data

US 2003/0134933 A1 Jul. 17, 2003

Related U.S. Application Data

(60) Provisional application No. 60/323,615, filed on Sep. 20, 2001.

(51) Int. Cl.
*A61C 5/00* (2006.01)
*A61K 6/083* (2006.01)
*C08K 3/30* (2006.01)
*C08F 4/40* (2006.01)

(52) U.S. Cl. .................. 433/228.1; 523/115; 523/116; 523/118; 523/120; 524/436; 526/222; 526/230

(58) Field of Classification Search ................ 523/115, 523/116, 118, 120; 536/222, 230; 433/228.1
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,715,331 A | 2/1973 | Molnar | |
| 3,751,399 A | 8/1973 | Lee | |
| 3,925,895 A * | 12/1975 | Kliment et al. | 433/224 |
| 3,926,906 A | 12/1975 | Lee | |
| 3,970,505 A | 7/1976 | Hauser | |
| 3,991,008 A | 11/1976 | Temin | |
| 4,515,910 A * | 5/1985 | Rawls et al. | 523/115 |
| 4,544,359 A | 10/1985 | Waknine | |
| 4,547,531 A | 10/1985 | Waknine | |
| 4,569,976 A | 2/1986 | Zimmerman | |
| 4,946,901 A * | 8/1990 | Lechner et al. | 525/305 |
| 5,043,361 A * | 8/1991 | Kubota et al. | 522/10 |
| 5,192,815 A * | 3/1993 | Okada et al. | 523/115 |
| 5,276,068 A | 1/1994 | Waknine | |
| 5,444,104 A | 8/1995 | Waknine | |
| 5,684,103 A | 11/1997 | Jia | |
| 5,705,581 A * | 1/1998 | Fife et al. | 526/248 |
| 6,068,852 A * | 5/2000 | Shah | 424/443 |
| 6,455,608 B1 * | 9/2002 | Jia et al. | 523/115 |
| 6,500,004 B2 * | 12/2002 | Jensen et al. | 433/228.1 |
| 6,624,211 B2 * | 9/2003 | Karim et al. | 523/116 |
| 2002/0120033 A1 | 8/2002 | Jia | |
| 2002/0123024 A1 | 9/2002 | Jensen | |

\* cited by examiner

*Primary Examiner*—Tae H Yoon
(74) *Attorney, Agent, or Firm*—Ann M. Knab

(57) ABSTRACT

A two-part self-curing endodontic sealing system comprises a thiourea derivative, such as acetyl thiourea, and a hydroperoxide, such as cumene hydroperoxide. The thiourea derivative is used as a reducing agent and the hydroperoxide is used as an oxidizing agent.

4 Claims, No Drawings

SELF-CURING SYSTEM FOR ENDODONTIC SEALANT APPLICATIONS

CROSS-REFERENCE TO RELATED APPLICATIONS

This application claims priority to U.S. Provisional Application No. 60/323,615, filed Sep. 20, 2001, which is incorporated herein by reference.

FIELD OF THE INVENTION

The present invention relates generally to compositions and methods for sealing a root canal during an endodontic procedure, and more specifically to sealing compositions having improved shelf-life stability.

BACKGROUND OF THE INVENTION

Conventional self-curing endodontic sealant composites use peroxide, mostly benzoyl peroxide (BPO) as the oxidant part of the redox initiator system. This system, consisting of BPO, in combination with a tertiary amine such as bis(2-hydroxyl)-p-toluidine (DHEPT), and dimethyl-p-toluidine (DMPT) as a reducing agent, can have sufficient curing time at room temperature. But BPO has a low half-life, resulting in poor shelf-life stability. Pastes containing BPO harden readily when stored at elevated temperatures. The self-curing of other peroxides with longer half-life, such as cumyl peroxide, t-butyl peroxide, initiated by an amine, is too slow to give a sufficiently rapid curing rate for acrylate resins.

Compositions based on polymerizable methacrylate monomers can be polymerized using hydroperoxide/thiourea redox systems, such as in U.S. Pat. No. 3,991,008 directed to dental compositions having improved color stability; U.S. Pat. No. 4,569,976 directed to a redox cure system for acrylic adhesive compositions; and U.S. Pat. No. 3,970,505 directed to anaerobic compositions and a surface activator therefore, all of which have hereby incorporated by reference.

These patents have not reported any stabilized paste formulations for the use in endodontic compositions. The studies were limited to room temperature conditions and no self-curing paste formulations at elevated temperatures of up to 60° C. were reported in any field.

It is desirable to provide a stable self-curing endodontic composition having a sufficient curing rate. It would be beneficial to provide an endodontic sealing composition having stable shelf life at high temperatures.

SUMMARY OF THE INVENTION

The above-described and other problems and deficiencies of the prior art are overcome or alleviated by the two-part self-curing endodontic sealing system of the invention. The sealing system provides a thiourea derivative, such as acetyl thiourea, and a hydroperoxide, such as cumene hydroperoxide. The thiourea derivative is used as a reducing agent and the hydroperoxide is used as an oxidizing agent. In the reducing component, an acidic methacrylate resin is used with the thiourea derivative to fasten the curing. At room temperature, this self-curing system can give a comparable working time and setting time as in the BPO-amine system, but with a much better shelf-life stability at elevated temperatures up to about 60° C. Also, under acidic or basic conditions with influences from various fillers and/or organic acids, this self-curing endodontic sealing composition shows an improved shelf-life stability compared to current BPO/amine systems. The composition herein is also useful as a dental cement.

DETAILED DESCRIPTION OF THE INVENTION

As will be appreciated, the invention provides a self-curing endodontic system with improved shelf-life stability compared to conventional benzoyl peroxide/amine systems. This composition contains a redox self-curing system comprising a hydroperoxide oxidizing agent and a thiourea derivative reducing agent. This new self-curing endodontic system is especially good for elevated temperatures up to 60° C. Also, it shows improved shelf-life stability under basic or acidic conditions, especially under influences of various fillers.

Hydroperoxide has the formula of R—OOH, where R is an aliphatic or an aromatic group. Examples of aliphatic and aromatic groups include, but are not limited to, alkyl and aryl groups. Specific examples include, but are not limited to, t-butyl, cumyl, p-methane or p-isopropyl cumyl. Thiourea derivatives can be N-substituted thiourea compounds having the formula $(R_1R_2N)C=S(NR_3R_4)$, where $R_1$, $R_2$, $R_3$, and $R_4$ can be H, a linear or cyclic alkyl, aryl, aralkyl, or allyl group. Examples include, but are not limited to phenyl-, acetyl- and ally-thiourea. In addition, an acidic component may be added into the thiourea part to give a sufficiently rapid redox reaction at room temperature. Any organic acids which are miscible with acrylate or methacrylate resins can be used. Preferred acids are acrylate or methacrylate resins with pendant acidic groups. Examples include, but are not limited to, methacrylic acid, pyromellitic dianhydrate glyceryl dimethacrylate (PMGDM), 4-methacryloxyethyl trimellitic anhydride (4-META) and any other acidic resins with carboxylic or phosphoric acid groups attached.

In one preferred embodiment herein, cumene hydroperoxide $C_6H_5C(CH_3)_2OOH$ (CHP) and acetyl thiourea $CH_3CONHCSNH_2$ (ATU) are used and methacrylic acid is optionally used as the acidic promoter. In another preferred embodiment herein, cumene hydroperoxide $C_6H_5C(CH_3)_2OOH$ (CHP) and allyl thiourea $CH_2{:}CHCH_2NHCSNH_2$ (ALTU) are used and methacrylic acid is optionally used as the acidic promoter.

Preferred resins include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") are also commonly-used principal polymers suitable for use in the present invention. Resins also include a biodegradable methacrylate such as polylactide methacrylate (PLAMA) which is a polymerization product of lactide with 2-hydroxyethyl methacrylate (HEMA) as disclosed in commonly assigned U.S. patent application Ser. No. 09/638,206 filed Aug. 11, 2000, and U.S. patent application Ser. No. 20,020,120,033, filed Dec. 5, 2001 and published Aug. 29, 2002, both of which are hereby incorporated by reference.

The compositions may further comprise at least one filler known in the art and used in dental restorative materials. Generally, the filler is added in an amount of up to about eighty percent by weight of each component in the two-component system. Suitable fillers are those capable of being covalently bonded to the polymeric matrix that forms from the resin itself or to a coupling agent that is covalently bonded to both. Examples of suitable filling materials include but are not limited to those known in the art such as silica, silicate glass, quartz, barium silicate, barium sulfate, barium molybdate, barium methacrylate, zirconium methacrylate, barium yttrium alkoxy ($Ba_2Y(OR)_x$), strontium silicate, barium borosilicate, strontium borosilicate, borosilicate, lithium silicate, amorphous silica, calcium phosphates such as calcium hydroxyapatite and amorphous calcium phosphate, calcium hydroxide, alumina, zirconia, tin oxide, tantalum oxide, niobium oxide, and titania. Particularly suitable fillers for dental filling-type materials prepared in accordance with this invention are those having a particle size ranging from about 0.1-5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and 4,547,531 to Waknine, the pertinent portions of which are incorporated herein by reference. Suitable organic filler materials are known in the art, including for example the poly(methacrylate) fillers described in U.S. Pat. No. 3,715,331 to Molnar. A mixture of organic and inorganic filler materials may also be used.

Additional components may be added to the two-part system, to each part, or to one part only. Additives include, but are not limited to, second polymerization initiators such as photoinitiators and redox initiators, polymerization inhibitors, stabilizers, photoinitiators, radiopaque materials, and therapeutic agents. The second redox initiator can be chosen from a conventional system such as, but not limited to, a BPO/amine system, perester or hydroperoxide/ascorbic acid or ascorbyl palmitate system, and (thio)barbitoric acid compound/copper or iron halide system. The amount of addition, however, should not be a primary factor in the initiation reaction, rather having a synergetic effect to accelerate the reaction.

Examples of inhibitors include, but are not limited to, butylated hydroxytoluene, hydroquinone, hydroquinone monomethyl ether, benzoquinone, chloranil, phenol, and the like. A preferred polymerization inhibitor is 2,6-di-tert-butyl-4-methylephenol (BHT). The inhibitor is used to scavenge small amounts of free radicals during storage and to improve the shelf stability of the sealing system. More than one inhibitor may be used in the system of the invention. For example, in a two paste system, both the catalyst paste and the base paste may contain a polymerization inhibitor. The polymerization inhibitor is preferably present in an amount up to about 3% by weight, preferably from about 0.001% to about 2% by weight, more preferably about 0.01% to about 0.5%.

Although the system herein is a self-curing system, it may be useful to include a photoinitiator in the system, to effect rapid curing in the upper portion of the sealing material within the root canal. The dentist may then place a composite resin on top of the sealing resin, to finish the restoration. Otherwise, the patient may have to wait until the curing has been fully effected for the dentist to finish the restoration with a permanent crown. Alternatively, the patient may be fitted with a temporary crown and return at a later date to be fitted with the permanent crown.

When the dentist is ready to use the system, the two components are mixed and inserted into the root canal after the gutta percha or similar material has been placed and prior to insertion of the post.

The following Table 1 sets forth ranges of the two-component system herein which is combined at the time of use wherein composition A is present in the range of about 20-80 percent by weight and composition B is present in the range of about 20-80 percent by weight, and preferably wherein composition A is present in an amount of about 50% by weight and composition B is present in an amount of about 50% by weight.

TABLE 1

Cumene Hydroperoxide (CHP) Paste Formulation/Acetyl Thiourea (ATU) Paste Formulation

| | Wt. % |
|---|---|
| Composition A | |
| Resin | about 10-about 60 |
| BHT-(2,6-di-tert-butyl-4-methylephenol) | about 0-about 0.2 |
| CHP | about 1-about 10 |
| Filler(s) | about 1-about 80 |
| Composition B | |
| Resin | about 10-about 60 |
| BHT | 0-about 0.2 |
| ATU | about 1-about 10 |
| Acrylate/methacrylate compatible organic acid | 0-about 20 |
| Filler(s) | about 1-about 80 |

The following examples illustrate the invention.

EXAMPLE 1

Preparation of CHP/ATU Pastes

CHP and ATU pastes were prepared using a methacylate resin and fillers. The resins are approximately a 60/40 weight ratio of BisGMA/TEGDMA. The formulation of these pastes are shown in Tables 2 and 3, respectively. A curing test of this self-curing system was performed at 22° C. by mixing 1:1 weight ratio of composition A: composition B shown in Tables 2 and 3 below.

TABLE 2

CHP Paste Formulation

| Composition A | Wt. % |
|---|---|
| Resin | 33 |
| BHT | 0.05 |
| CHP | 1 |
| Glass Filler | 66 |

TABLE 3

ATU Paste Formulation

| Composition B | Wt. % |
|---|---|
| Resin | 33 |
| BHT | 0.03 |
| ATU | 1 |
| Methacrylic acid | 3.3 |
| $Ca_3(PO_4)_2$ | 31.5 |
| $BaSO_4$ | 31.5 |

Gel time and setting time of the above combination in a 1:1 ratio at 22° C. were 4 minutes and 30 seconds and 6 minutes and 30 seconds, respectively.

Comparative Example 2

Preparation of Benzoyl Peroxide BPO/Bis(2-Hydroxyl)-P-Toluidine DHEPT Pastes

A similar composition as in Example 1 was prepared using a BPO/amine system. The resins used in this example were the same as those used in Example 1. BPO and DHEPT pastes were prepared as set forth in Tables 4 and 5, respectively.

TABLE 4

BPO Paste Formulation

| Composition | Wt. % |
|---|---|
| Resin | 33 |
| BHT | 0.05 |
| BPO | 1 |
| Glass Filler | 66 |

TABLE 5

DHEPT Paste Formulation

| Composition | Wt. % |
|---|---|
| Resin | 33 |
| BHT | 0.03 |
| DHEPT | 0.6 |
| $Ca_3(PO_4)_2$ | 33.4 |
| $BaSO_4$ | 33 |

Gel time and setting time of the above pastes were 2 minutes 30 seconds and 3 minutes 40 seconds, respectively.

Shelf-life Stability Comparison of Example 1 and Comparative Example 2

Shelf-life stability of the composition of Example 1 and the composition of Comparative Example 2 was tested at different temperatures. Gel time and setting time are listed in Table 6 for CHP/ATU and BPO/DHEPT.

TABLE 6

Aging Test of CHP/ATU at Different temperature

| Temperature | Aging Time (week) | Gel Time/Setting Time CHP/ATU System (Example 1) | Gel Time/Setting Time BPO/DHEPT System (Comparative Example 2) |
|---|---|---|---|
| 37° C. | 0 | 4 min 30 sec/6 min 10 sec | 2 min 30 sec/3 min 40 sec |
| | 1 | 4 min 00 sec/5 min 30 sec | 1 min 30 sec/2 min 20 sec |
| | 2 | 4 min 00 sec/5 min 30 sec | 1 min 20 sec/2 min 10 sec |
| | 3 | 4 min 10 sec/5 min 10 sec | 1 min 30 sec/2 min 20 sec |
| | 4 | 3 min 50 sec/5 min 00 sec" | 1 min 40 sec/2 min 20 sec |
| 50° C. | 0 | 4 min 30 sec/6 min 10 sec | BPO-containing paste hardened in two days |
| | 1 | 4 min 00 sec/5 min 30 sec | |
| | 2 | 4 min 50 sec/6 min 20 sec | |
| | 3 | 6 min 30 sec/8 min 30 sec | |
| | 4 | 6 min 30 sec/8 min 30 sec | |
| 60° C. | 0.5 | 5 min 10 sec/7 min 30 sec | BPO-containing paste hardened in a couple of hours |
| | 1 | both CHP and ATU pastes gelled | |

The results in Table 6 show a stabilized formula of the CHP/ATU system in 4 weeks at 37° C. Compared to the BPO/DHEPT system at elevated temperatures, in which the BPO paste gelled in two days at 50° C. and in a couple of hours at 60° C., the CHP/ATU system showed a much better stability. At 50° C., the CHP paste did not gel after 4 weeks. The curing time after 4 weeks was a little slower, but it still showed good curability. At 60° C., this system also showed a good curability for three days.

Example 3

Self-Curing System Under Acidic Conditions

A biodegradable polylactide methacrylate PLAMA was used in this example. It was formulated with CHP/ATU as well as with BPO/DHEPT. The PLAMA resin contains some lactic acid due to its synthetic methods, and also releases lactic acid during its degradation. The resin used in both systems was 70/30 by weight of PLAMA/TEGMA. Table 7 shows the formulation of the base (oxidant) and catalyst (reductant) compositions.

Table 7. BPO/DHEPT and CHP/ATU Self-curing System Paste Formulation

| Component | Resin | $BaSO_4$ | TCP | BHT | DHEPT or ATU | BPO or CHP |
|---|---|---|---|---|---|---|
| DHEPT Base | 59% | 20% | 20% | 0.06% | 1% | — |
| ATU Base | 57% | 20% | 20% | 0.06% | 3% | — |
| BPO Catalyst | 58.2% | 20% | 20% | 0.06% | — | 1.8% |
| CHP Catalyst | 57% | 20% | 20% | 0.06% | — | 3% |

Aging studies were performed for both systems at room temperature and 37° C. Gel time and setting time for the above formulations were tested for the aged using the same methods as described in Example 1. Aging test results were shown in Table 8.

TABLE 8

Aging Test of CHP/ALTU and BPO/DHEPT systems

| Temperature | Aging Time (week) | Gel time/Setting Time (min) (CHP/ATU system) | Gel time/Setting Time (min) (BPO/DHEPT system) |
|---|---|---|---|
| Room Temperature | 0 | 5 min 30 sec/7 min 40 sec | 7 min 50 sec/10 min 00 sec |
| | 1 | 4 min 00 sec/5 min 20 sec | 7 min 30 sec/8 min 30 sec |
| | 2 | 3 min 00 sec/4 min 40 sec | 7 min 40 sec/9 min 00 sec |
| | 3 | 2 min 55 sec/4 min 35 sec | 8 min 30 sec/10 min 20 sec |
| | 4 | 3 min 30 sec/5 min 30 sec | 8 min 40 sec/10 min 50 sec |
| | 6 | 3 min 30 sec/5 min 40 sec | 9 min 30 sec/12 min 00 sec |
| 37° C. | 0 | 5 min 30 sec/7 min 40 sec | 7 min 50 sec/10 min 00 sec |
| | 1 | 3 min 00 sec/4 min 45 sec | 10 min 10 sec/12 min 10 sec |
| | 2 | 3 min 00 sec/4 min 40 sec | 11 min 20 sec/13 min 50 sec |
| | 3 | 3 min 00 sec/4 min 40 sec | 11 min 30 sec/14 min 00 sec |
| | 4 | 2 min 40 sec/4 min 20 sec | 14 min 30 sec/18 min 00 sec |
| | 6 | 2 min 50 sec/4 min 30 sec | 14 min 40 sec/18 min 10 sec |

The results in Table 8 show a more stable formulation when using CHP/ATU self-curing system comparing to BPO/DHEPT, in which both gel time and setting time slowed with time especially at 37° C. for the BPO/DHEPT system.

Example 4

Self-Curing System Under Basic Conditions

This system was designed for slow curing under basic conditions using a basic filler, calcium hydroxide, in the base of the formulation. The catalysts, CHP paste and BPO paste formulations, are the same as in Example 1 and Example 2, respectively. In the thiourea derivative part base, allyl thiourea (ALTU) was used as the reductant instead of acetyl thiourea (ATU). No acidic promoter was added in this formulation. The resins used were UDMA/TEGMA 60/40 for both ALTU and DHEPT base formulations. Table 9 shows the compositions for ALTU and DHEPT base pastes, respectively.

TABLE 9

Base (ALTU or DHEPT) Paste Formulation

| Composition B | Wt. % |
|---|---|
| Resin | 33 |
| BHT | 0.03 |
| Base (ALTU or DHEPT) | 0.3 |
| Silane treated barium glass filler | 11.7 |
| Ca(OH)2 | 15 |
| BaSO$_4$ | 40 |

An aging study was performed for both systems at room temperature and 37° C. The setting time was used to evaluate the curing behavior. The same weight of the two parts were mixed together and put in between two microslides. Setting time was measured as the time when the two slides were not movable. The results are shown in Table 10.

Table 10. Aging Test of CHP/ALTU and BPO/DHEPT System

| Temperature | Aging Time (week) | Setting Time (min) (CHP/ALTU system) | Setting Time (min) (BPO/DHEPT system) |
|---|---|---|---|
| RT | 0 | 25 | 17 |
| | 1 | 27 | 26 |
| | 2 | 26 | 33 |
| | 3 | 35 | 45 |
| | 4 | 33 | 57 |
| 37° C. | 0 | 25 | 17 |
| | 1 | 27 | 40 |
| | 2 | 28 | 55 |
| | 3 | 29 | 75 |
| | 4 | 29 | >120 |

As shown in Table 10, for this slow reaction under basic conditions, the CHP/ALTU system exhibits a much more stable shelf-life than BPO/DHEPT system.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of sealing a root canal during an endodontic procedure using a sealing composition comprising:
    mixing a first part of the sealing composition comprising a hydroperoxide oxidizing agent in an amount from about 1% to 3% by weight with a second part of the sealing composition comprising a thiourea reducing agent in an amount from about 1% to 3% by weight, wherein the second part further comprises an acidic component, wherein a polymerizable resin is contained in at least the first part or the second part of the sealing composition, wherein the sealing composition comprises a basic filler consisting essentially of calcium hydroxide; and wherein the sealing composition is shelf-life stable at 50° C. for about four weeks; and inserting the sealing composition into the root canal.

2. The method of claim 1 wherein the acidic component comprises an organic acid miscible in the polymerizable resin.

3. The method of claim 2 wherein the organic acid comprises an acid having a carboxylic or phosphoric acid group attached.

4. The method of claim 2 wherein the organic acid comprises methacrylic acid, pyromellitic dianhydrate glyceryl dimethacrylate (PMGDM), or 4-methacryloxyethyl trimellitic anhydride (4-META).

* * * * *